(12) United States Patent
Jin

(10) Patent No.: US 10,515,461 B2
(45) Date of Patent: Dec. 24, 2019

(54) REFERENCING SYSTEM

(71) Applicant: Purdue Research Foundation, West Lafayette, IN (US)

(72) Inventor: Jian Jin, Lafayette, IN (US)

(73) Assignee: Purdue Research Foundation, West Lafayette, IN (US)

(*) Notice: Subject to any disclaimer, the term of this patent is extended or adjusted under 35 U.S.C. 154(b) by 0 days.

(21) Appl. No.: 16/038,161

(22) Filed: Jul. 17, 2018

(65) Prior Publication Data

US 2019/0019310 A1   Jan. 17, 2019

Related U.S. Application Data

(60) Provisional application No. 62/533,587, filed on Jul. 17, 2017.

(51) Int. Cl.
 *G06T 7/80* (2017.01)
(52) U.S. Cl.
 CPC ...... *G06T 7/85* (2017.01); *G06T 2207/10024* (2013.01); *G06T 2207/10028* (2013.01)

(58) Field of Classification Search
 CPC ............. G06T 7/85; G06T 2207/10028; G06T 2207/10024; G01J 3/00; G01J 3/0297; G01N 21/274; H04N 5/20
 See application file for complete search history.

(56) References Cited

U.S. PATENT DOCUMENTS

| | | | |
|---|---|---|---|
| 10,155,346 B1* | 12/2018 | Gorgi | B33Y 10/00 |
| 2018/0186082 A1* | 7/2018 | Randhawa | B29C 64/135 |
| 2018/0290365 A1* | 10/2018 | Noorazar | B29C 64/118 |
| 2018/0361729 A1* | 12/2018 | Gibson | B33Y 30/00 |
| 2019/0111642 A1* | 4/2019 | Chang | B29D 11/00663 |

* cited by examiner

*Primary Examiner* — Oschta I Montoya
(74) *Attorney, Agent, or Firm* — Purdue Research Foundation

(57) ABSTRACT

A reference imaging system including a planar reference piece. The reference imaging system further includes a three-axis gantry for positioning the planar reference piece at a plurality of points in a 3D coordinate system. Additionally, the reference imaging system includes a yaw actuator for adjusting the yaw angle of the object. Furthermore, the reference imaging system includes a pitch actuator for adjusting the pitch of the object. Moreover, the reference imaging system includes a computer processing unit for controlling the 3D position, pitch and yaw of the planar reference piece.

6 Claims, 9 Drawing Sheets

Effect of leaf angle on reflectance

Surface angle is a major input to PROSAIL model

Effect of leaf angle on reflectance

Surface angle is a major input to PROSAIL model

800nm band standard deviation:
Use flat white: 0.2798
Use slope white: 0.0644

1. White reference piece
2. White reference piece connector
3. Pitch axis motor
4. Yaw axis module
5. Yaw axis motor
6. Y axis linear gantry
7. Y axis motor
8. Y-X connector
9. X axis linear gantry
10. X axis motor
11. Z axis linear gantry
12. Z axis motor
13. Base 1. White reference strip
2. White reference strip connector
3. Pitch or yaw axis motor
4. T axis linear module
5. T axis motor
6. Vertical-horizontal rotator
7. Vertical-horizontal motor
8. Z connector
9. Z axis linear module
10. Z axis motor
11. Base 1. White reference semi-sphere
2. White reference connector
7. Y-Z axis connector
8. Z axis module
9. Z axis motor
10. Base 1. White reference semi-sphere
2. White reference connector
3. Y axis module
4. Y axis motor
5. X axis module
6. X axis motor
7. X-Z axis connector
7. Z axis module
8. Z axis motor
9. Base

REFERENCING SYSTEM

TECHNICAL FIELD

The present application relates to 3D object imaging, and more specifically, to a referencing system for general imaging including hyperspectral imaging, RGB imaging, grey-scale imaging etc.

BACKGROUND

Image calibration with white referencing is one important step of scientific imaging. The goal of the calibration is to eliminate the impact from uneven lighting conditions. Typically, shortly before or after the raw image of the target object is taken, a white tile is placed at the same position as the object and is imaged too. For each image pixel, the pixel value in the raw image is divided by the corresponding pixel value of the white reference image:

> Corrected Image from the camera=Image of sample/
> Image of white tile

Sometimes the dark reading image is also taken by closing the aperture or simply putting on the lens cover, in which case:

> Corrected Image from the camera=(Image of
> sample−Dark reading Image)/(Image of white
> tile−Dark reading Image)

The above method works well for flat objects, but when the object has complicated 3D shapes this method has serious problems because 1) the object surface may be at different depth distances from the camera, where the lighting intensity can differ a lot from where the flat white tile is located, and 2) the object surface may be at many different tilted angles, which will severely change the reflectance not only in intensity, but also in color. Take plant leaf reflectance for example, where the PROSAIL model (http://teledetection.ipgp.jussieu.fr/prosail/) shows the different leaf angles completely change the reflectance spectra, which may cause 300% change in color index calculation such as NDVI, as shown in FIG. 1.

The problem may be solved by replacing the flat white tile with a 3D white referencing. The 3D white reference should have exactly the same size and 3D shape as the target object. Since each target object is different, one solution can be achieved by placing a 3D scanner and a 3D printer on the spot. Every time a new object arrives, it is scanned by the 3D scanner. The scanning result is then sent to the 3D printer immediately to print out the 3D white reference. This 3D white reference is then scanned for the white reference image, which is used to calibrate the raw image of the object. Preliminary data from experiments confirm the improved calibration quality with 3D reference compared with 2D flat reference. FIG. 2 shows the spectra of multiple points on a 3D object calibrated with 3D and flat references separately. The object is made of uniform material and color, so the difference in spectra between the different points can only be from lighting and angle variation. As observed from the figure, the 3D reference did a far better job than the flat reference. In addition, plant leaves were also imaged, rotated by different angles. The result in FIG. 3 shows the similar improved calibration quality of 3D (sloped) reference compared with flat reference.

However, producing the 3D white reference for each object is an expensive and impractical approach, incurring increased processing time and resources. Therefore, improvements are needed in the field.

BRIEF DESCRIPTION OF THE DRAWINGS

One or more embodiments are illustrated by way of example, and not by limitation, in the figures of the accompanying drawings, wherein elements having the same reference numeral designations represent like elements throughout. It is emphasized that, in accordance with standard practice in the industry, various features may not be drawn to scale and are used for illustration purposes only. In fact, the dimensions of the various features in the drawings may be arbitrarily increased or reduced for clarity of discussion.

DETAILED DESCRIPTION

In the following description, some aspects will be described in terms that would ordinarily be implemented as software programs. Those skilled in the art will readily recognize that the equivalent of such software can also be constructed in hardware, firmware, or micro-code. Because data-manipulation algorithms and systems are well known, the present description will be directed in particular to algorithms and systems forming part of, or cooperating more directly with, systems and methods described herein. Other aspects of such algorithms and systems, and hardware or software for producing and otherwise processing the signals involved therewith, not specifically shown or described herein, are selected from such systems, algorithms, components, and elements known in the art. Given the systems and methods as described herein, software not specifically shown, suggested, or described herein that is useful for implementation of any aspect is conventional and within the ordinary skill in such arts.

Figure 1:
FIG. 1 illustrates effect of leaf angle of reflectance.
Figure 1:
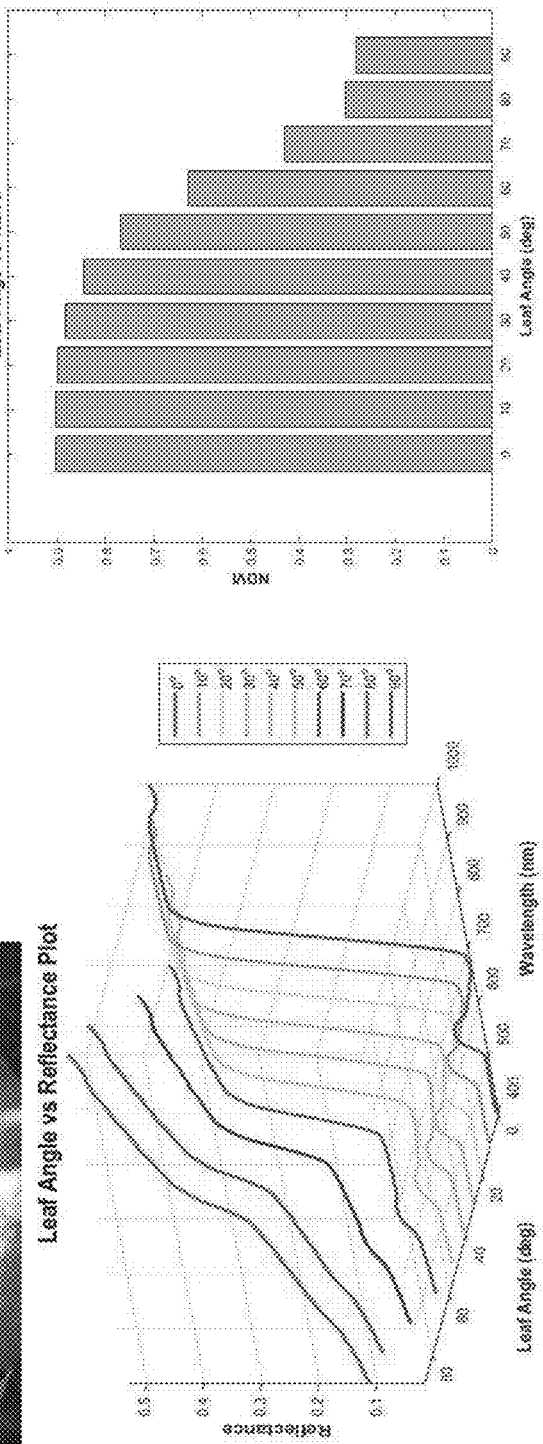
Figure 2:
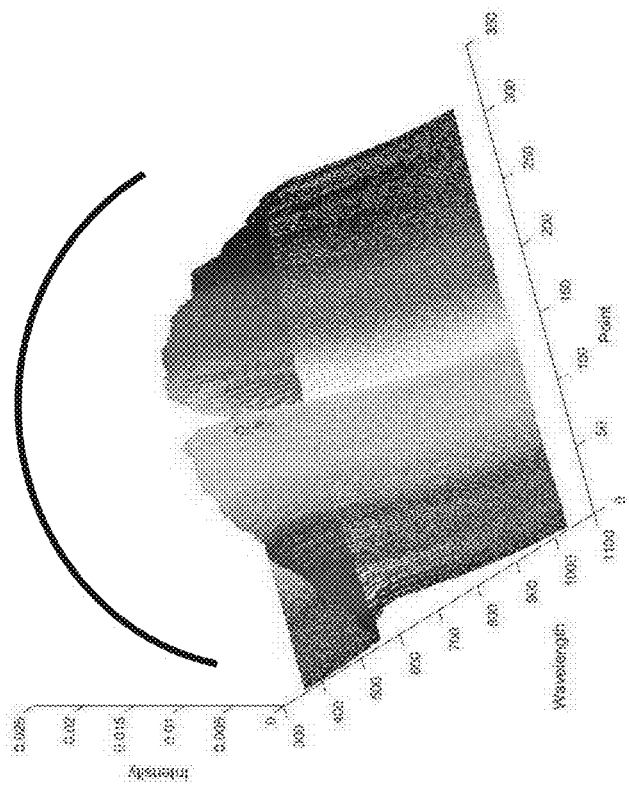
FIG. 2 illustrates a spectra of multiple points on a 3D object calibrated with 3D and flat references separately
Figure 2:
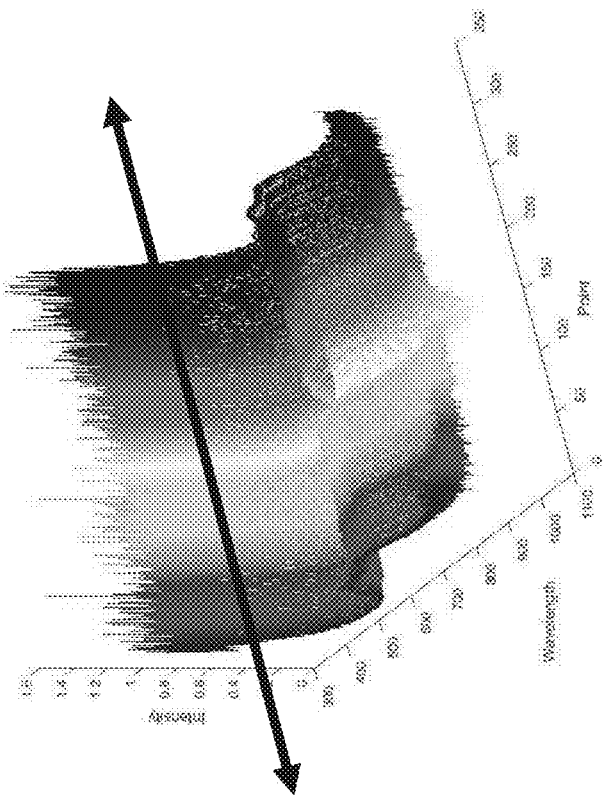
Figure 3:
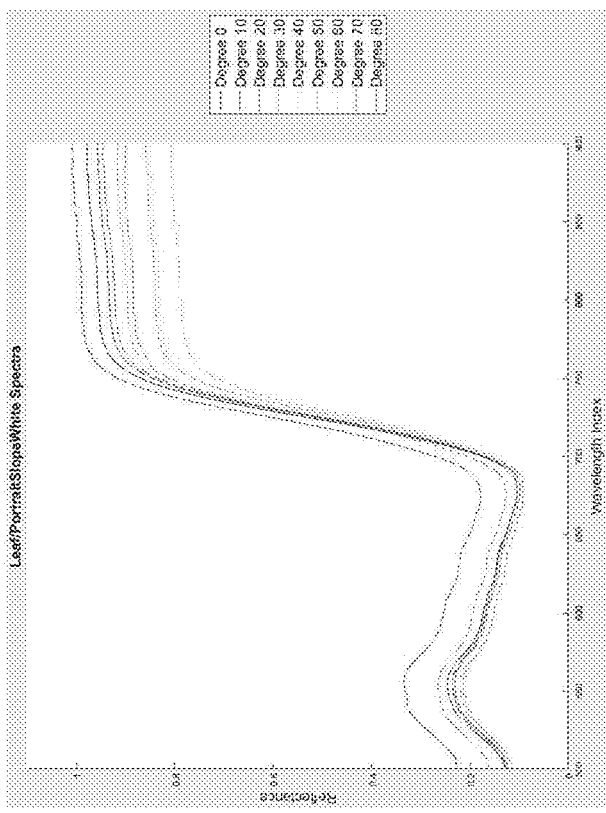
FIG. 3 illustrates improved calibration quality of 3D (sloped) reference compared with flat reference
Figure 3:
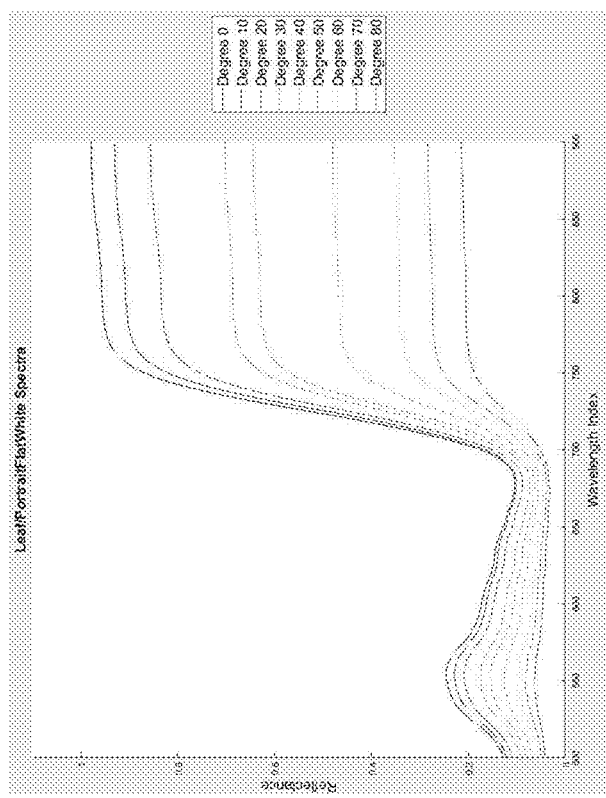
Figure 4:
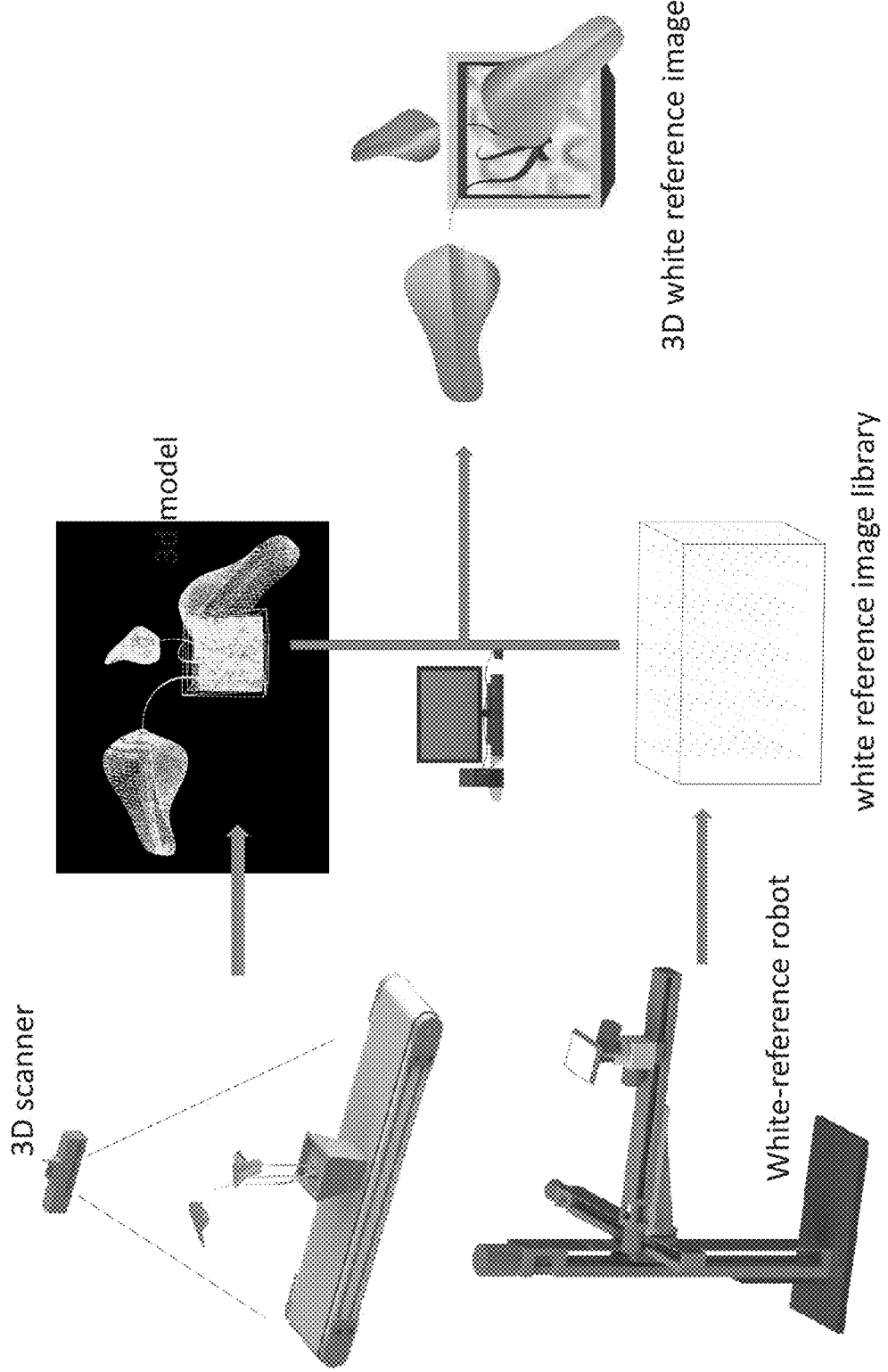
FIG. 4 illustrates a referencing system in accordance with one or more embodiments.
Figure 5:
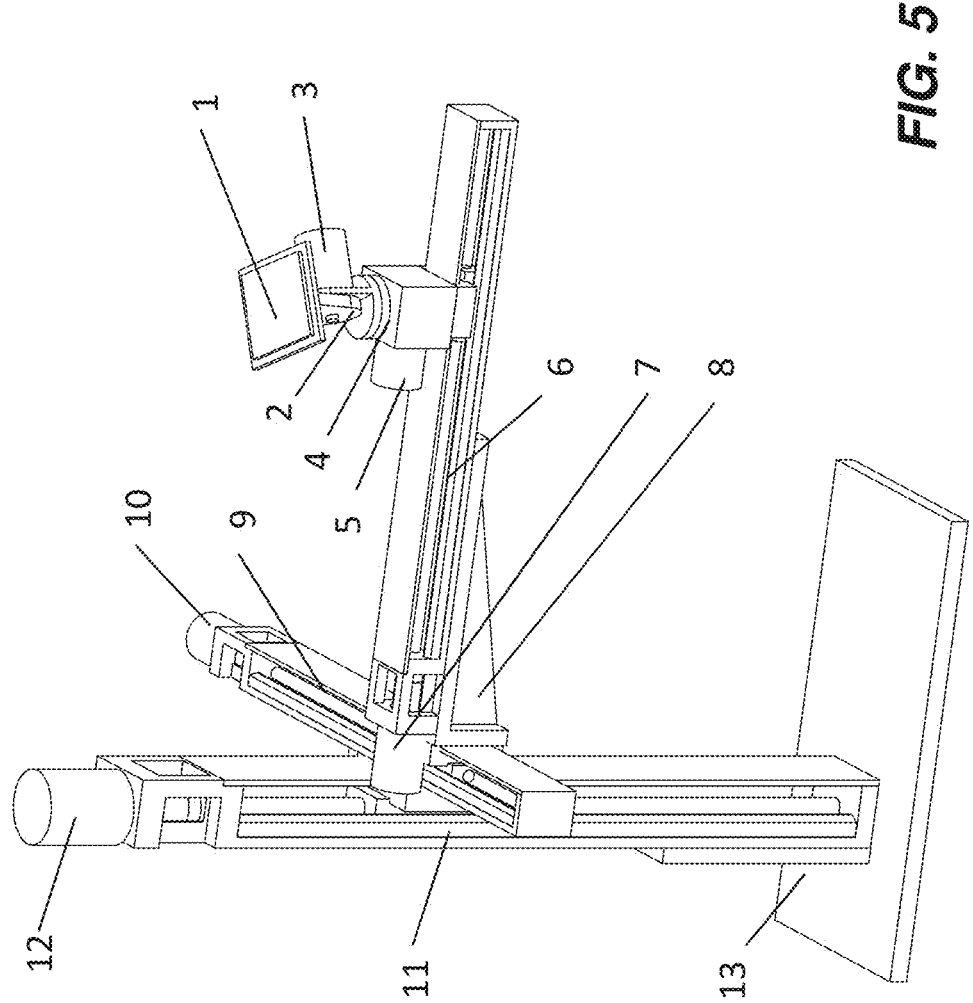
FIG. 5 illustrates a multi-axis moving apparatus in accordance with one or more embodiments.
Figure 6:
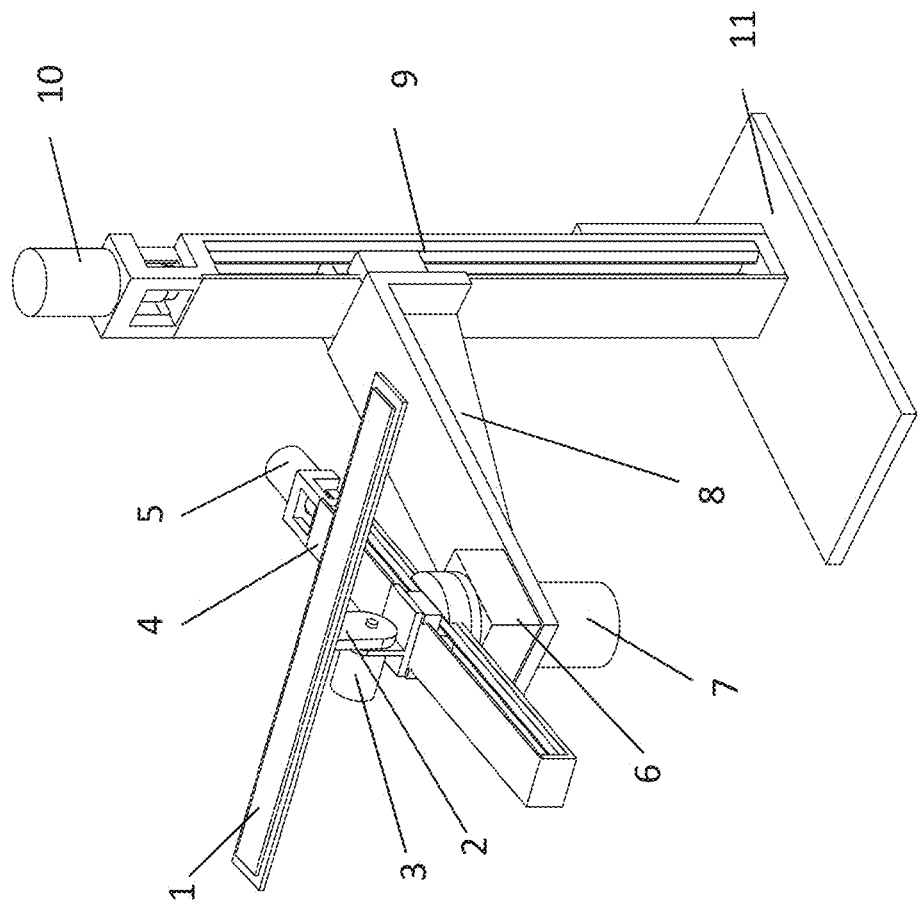
FIG. 6 illustrates a multi-axis moving apparatus in accordance with one or more embodiments.
Figure 8:
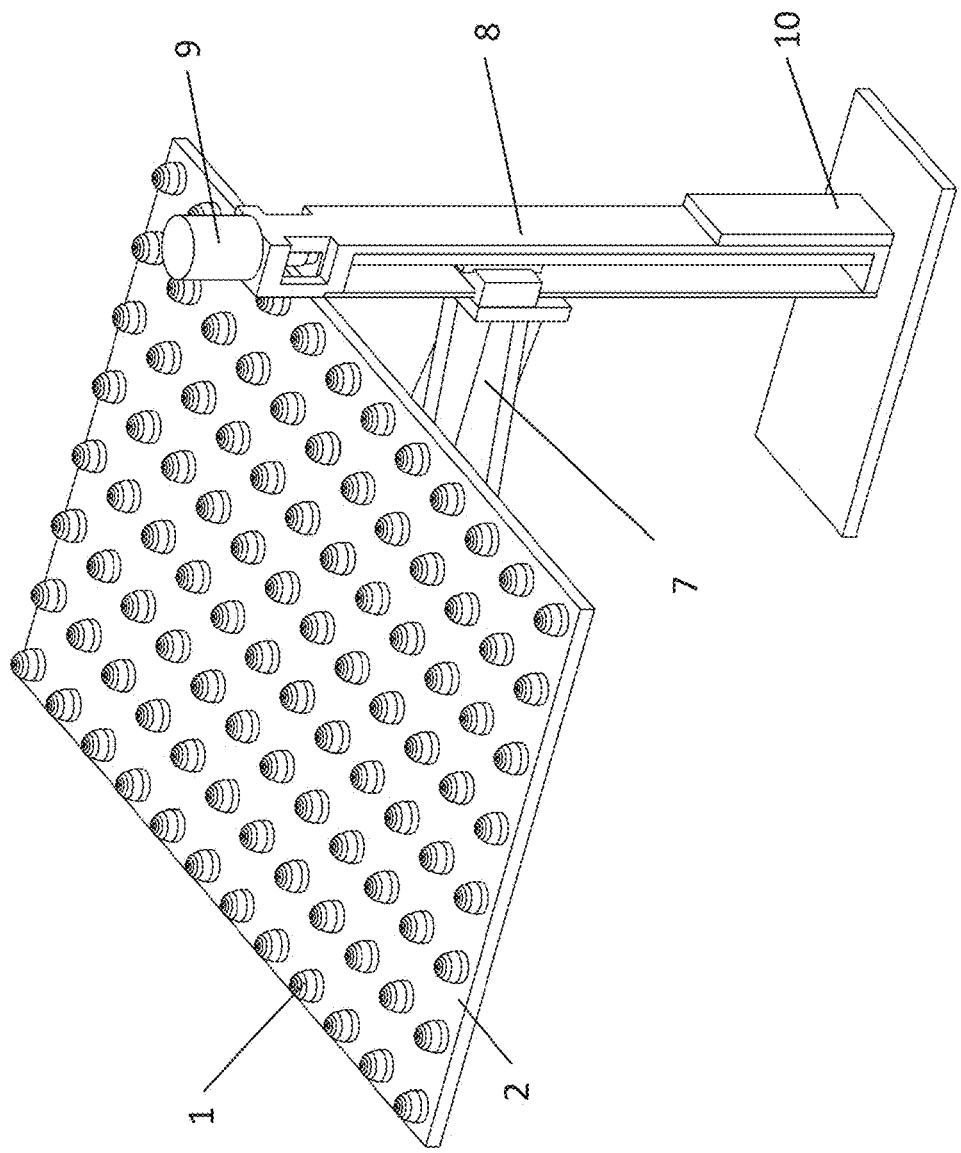
FIG. 8 illustrates a multi-axis moving apparatus in accordance with one or more embodiments.

The present disclosure provides a referencing system which calibrates images. The referencing system includes a multi-axis moving apparatus (e.g. FIGS. 5, 6, and 8) that has a reference piece mounted. In FIG. 5, the reference piece has a dimension that is greater than a dimension of a pixel. In FIG. 6, the reference piece has a dimension such that an entirety of a target object is contained within the length of the reference piece. In FIG. 8, the reference piece has a dimension such that an entirety of the target object is contained within a planar cross-section of the reference piece. The referencing system further includes a camera and a 3D scanner. In some embodiments, the camera includes an RGB camera or a hyperspectral camera. In at least one embodiment, the 3D scanner includes a 3D surface scanner, TOF camera, stereo camera, or a LiDAR.

In operation, step 1 begins with the referencing system collecting and storing a library of images of the reference piece at a multitude of positions and slope angles using the camera and the 3D scanner. In at least one embodiment, step 1 includes collecting a library of images of all possible locations, orientations, and slopes of the reference piece. The library is stored in a processing unit such as a computer. In step 2, a target object is scanned by the camera and the 3D scanner, thereby producing a camera image and a 3D scanner image, respectively. The target object can include a plant, a piece of meat, sculpture, or any 3D object. In step 3, each pixel from the camera image is matched with a corresponding pixel in the 3D scanner image so as to determine a 3D location, orientation, and slope of this pixel in the camera image. In one or more embodiments, step 3 is performed by the processing unit such as a computer. This step results in determination of location, orientation, and slope of all pixels in camera image, according to at least one embodiment.

In step 4, the determined 3D locations, orientations, and slopes of various pixels in the camera image are used to identify relevant corresponding images within the library. The relevant corresponding images within the library have locations, orientations and slopes that are commensurate with the determined 3D locations, orientations and slopes of various pixels of the camera image. In one or more embodiments, step 4 is performed by the processing unit such as a computer. In step 5, the relevant corresponding images are then used to virtually reconstruct a 3D reference image of the target object. In one or more embodiments, step 5 is performed by the processing unit such as a computer. In step 6, the camera image taken from the camera is calibrated based on the reconstructed 3D reference image. In one or more embodiments, the calibration includes using the 3D reference image to reference the camera image. In one or more embodiments, step 6 is performed by the processing unit such as a computer.

The reference platform automatically generates the reference image library. FIG. 5 illustrates one embodiment having a multi-axis movement apparatus, upon which a reference piece is mounted as shown. The platform includes an x-axis gantry and motor, a y-axis gantry and motor, a z-axis gantry and motor, a yaw axis motor, and a pitch axis motor and a mounting base as illustrated. To build the image library, the white reference piece is moved to each location and angle to be scanned by the 3D scanner. The illustrated embodiment provides a 5 degrees of freedom (DOF) robotic arm holding a white reference. The 3 motor driven linear gantries move the white tile to each x-y-z position, while the pitch and yaw axis motors rotate the white piece to each combination of pitch and yaw angles. The movement and rotation are controlled by the computer processing unit and synchronized with the imager. In this way the system automatically takes an image of the white reference piece at each position and angle, thereby constructing and storing the library of white reference images.

In one or more embodiments, the system of FIG. 5 first collects the white reference library data with proper spatial and angular resolutions in the imaging space. This only needs to be done periodically (up to several months, for example) until the lighting, mechanical structure, and camera setting have noticeable changes. To collect the white reference data, the system moves the tile to each of the coordinate positions in the x,y,z system, and each yaw and pitch angles. At each position, the system records an image of the tile and the associated reflectance data. Next, the 3D scanner is calibrated so the computer processing unit is able to match each original pixel with a 3D depth pixel. Next, the system uses the library to 3D reference the images in imaging arrays. The system records the image of the object and records a 3D scan of the object. At each 3D pixel, besides reading the (x, y, z) information, the system also calculates the direction (pitch and yaw angels) of the object surface at the point. This can be quickly done by a using a surface regression algorithm, for example. Then, for each original pixel, the system checks the x,y,z, pitch, yaw angels data with the matching 3D pixel (by the algorithm above), and uses that data to look up the white tile's reflection at the same position and direction from the library, and use that to reference the original value of that pixel.

Once drawback of the embodiment shown in FIG. 5 is the long time it takes to construct the entire library. For example, assuming a 1 cubic meter imaging space, and 50 mm desired special resolution and 10 degrees angle resolution for the image library, it requires taking $20^3*18^2=2,592,000$ images. With a normal push broom hyperspectral camera system, each scanning cycle takes about 10 seconds, so the total scanning duration will be about 300 days nonstop. Of course, the imaging time may be reduced by using a lower resolution, but at the expense of image quality.

FIG. 6 shows a further embodiment of a white referencing system for push broom line scanning hyperspectral imaging systems. The illustrated embodiment reduces the 5 DOF to 3 DOF, thereby dramatically increasing speed: The embodiment utilizes a white reference strip instead of a white piece so the imager can take an image of multiple pixels at a time; the white strip will be placed both horizontally and vertically, and only a single rotating motor is needed for both yaw and pitch angles, depending on the direction of the white strip. In the same example above, the total scanning time becomes $20^2*18*2=14,400$ images or 40 hours, which is 180 times faster than the embodiment of FIG. 5. Although 40 hours is still long, this procedure is only needed once for every imaging period of 1-2 months for instance. In operation, the embodiment of FIG. 6 positions the white reference tile strip to both horizontal and vertical directions. At each direction, the tile strip is moved to each of the x and z positions in the coordinate system, and rotates the tile strip to each of the angles for pitch and yaw. The image data and associated reflectance is then recorded. The remainder of the process is the same as described with respect to the embodiment of FIG. 5.

Figure 7:
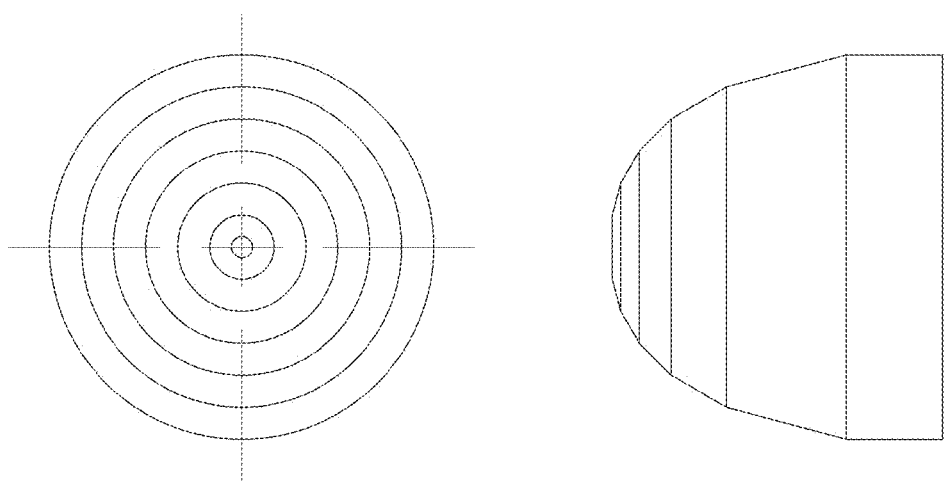
FIG. 7 illustrates a reference semi-sphere.

FIGS. 7 and 8 show a further embodiment, which includes a plurality of semispherical white reference objects mounted on a panel as shown. The grid of semispherical reference objects are distributed on the panel, and each semispherical object provides references at a plurality of different angles. In this way, the original 5 DOF requirement is reduced to only 1 DOF (we only need to move the panel up and down at different heights), thereby reducing the total processing time to a matter of minutes. In operation, the embodiment of FIGS. 7 and 8 move the tile to each of the z positions. At each z position, and image the panel and associated reflectance data are recorded. The spatial resolution of the white reference library depends on the density of the sphere array. In order to increase this resolution, the array panel can slide in both x and y directions in certain embodiments to locate the spheres at different positions and repeat this step again for several iterations. The remainder of the process is the same as described with respect to the embodiment of FIG. 5.

Figure 9:
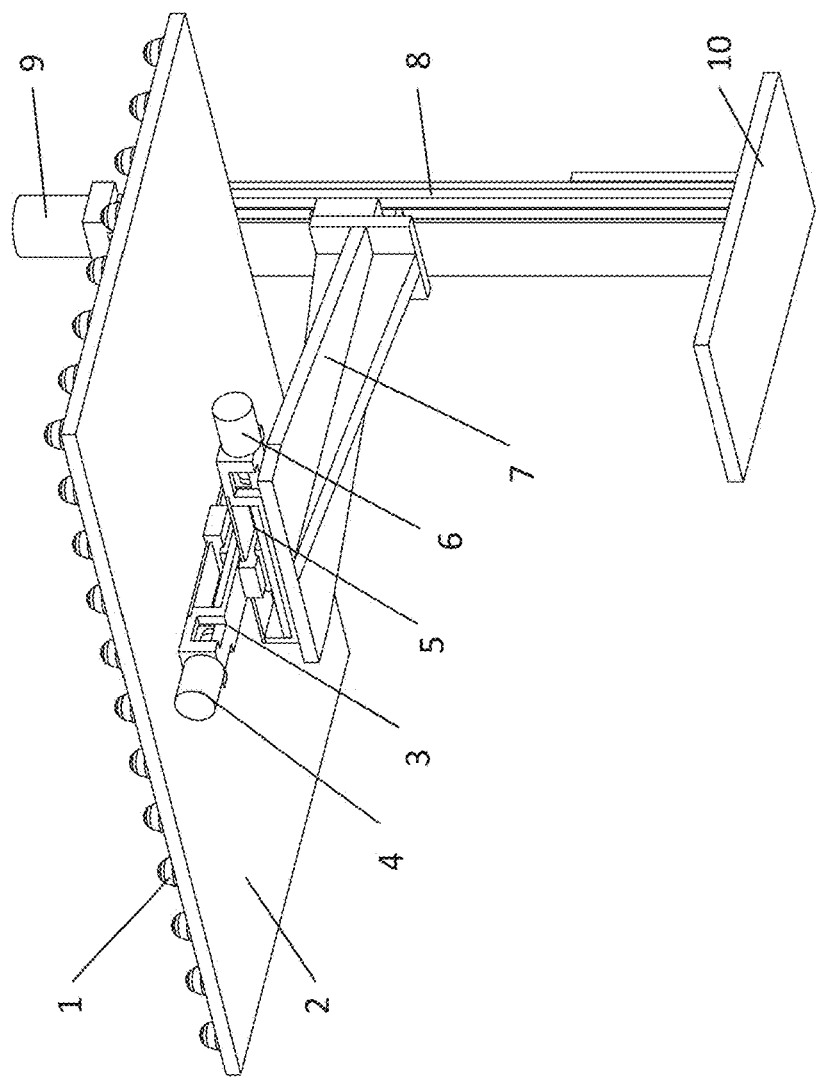
FIG. 9 illustrates a multi-axis moving apparatus in accordance with one or more embodiments.

The spatial resolution of the embodiment of FIGS. 7 and 8 is the distance between 2 neighboring semi-sphere reference objects. If higher resolution is needed, 2 motors can be added to enable the movement in x and y directions as shown in FIG. 9. This will provide any spatial resolution needed, but it should not increase the scanning time too much since the maximum moving distance is just the distance between 2 neighboring semispherical white reference objects. In various embodiments, each of the semisphere reference objects are coated with polytetrafluoroethylene, PVC, or a polymer. In one or more embodiments, each of the semi-sphere reference objects can have any other color except for black. In some embodiments, each of the semi-sphere reference objects are white in color.

The invention is inclusive of combinations of the aspects described herein. References to "a particular aspect" and the like refer to features that are present in at least one aspect of the invention. Separate references to "an aspect" (or "embodiment") or "particular aspects" or the like do not necessarily refer to the same aspect or aspects; however, such aspects are not mutually exclusive, unless so indicated or as are readily apparent to one of skill in the art. The use of singular or plural in referring to "method" or "methods" and the like is not limiting. The word "or" is used in this disclosure in a non-exclusive sense, unless otherwise explicitly noted.

The invention has been described in detail with particular reference to certain preferred aspects thereof, but it will be understood that variations, combinations, and modifications can be effected by a person of ordinary skill in the art within the spirit and scope of the invention.

The invention claimed is:

1. A reference imaging system, comprising:
    a panel having a plurality of reference objects mounted thereon;
    a single-axis gantry for positioning the panel at a plurality of points in a 3D coordinate system;
    a yaw actuator for adjusting the yaw angle of the panel;
    a pitch actuator for adjusting the pitch of the panel; and
    a computer processing unit for controlling the 3D position, pitch and yaw of the panel;
    wherein the computer processing unit records the reflectance data of the objects at the plurality of points;
    wherein the computer processing unit compares the reflectance data of the plurality of reference objects with reflectance data of a sample to determine a corrected image of the sample.

2. The system of claim 1, wherein the plurality of reference objects are semispherical in shape.

3. The system of claim 1, further comprising an imager for recording images and reflectance data of the objects.

4. The system of claim 1, wherein each reference object of the plurality of reference objects comprises any color except for black.

5. The system of claim 1, wherein each reference object of the plurality of reference objects is coated with PVC, polymer, or polytetrafluoroethylene.

6. The system of claim 1, wherein the panel has a dimension such that an entirety of the target object is contained within a planar cross-section of the reference piece.

* * * * *